(12) United States Patent
Diermann et al.

(10) Patent No.: US 7,141,023 B2
(45) Date of Patent: Nov. 28, 2006

(54) MICRO PERFUSION DEVICE COMPRISING A COLLECTING CONTAINER

(75) Inventors: Ulrich Diermann, Ipsach (CH); Ulrich Haueter, Grosshochstetten (CH)

(73) Assignee: Disetronic Licensing AG, Burgdorf (CH)

( * ) Notice: Subject to any disclaimer, the term of this patent is extended or adjusted under 35 U.S.C. 154(b) by 370 days.

(21) Appl. No.: 10/225,557

(22) Filed: Aug. 21, 2002

(65) Prior Publication Data

US 2003/0047011 A1 Mar. 13, 2003

Related U.S. Application Data

(63) Continuation of application No. PCT/CH01/00111, filed on Feb. 22, 2001.

(30) Foreign Application Priority Data

Feb. 22, 2001 (DE) ................. 100 08 826

(51) Int. Cl.
- A61B 5/00 (2006.01)
- A61M 3/00 (2006.01)
- A61M 5/178 (2006.01)
- B65D 81/00 (2006.01)

(52) U.S. Cl. .................. 600/573; 600/584; 604/43; 604/44; 604/164.01

(58) Field of Classification Search ............... 600/573, 600/576, 578, 580, 581, 309, 584; 604/27, 604/36, 37, 40, 43, 44, 164.01, 164.02, 164.06, 604/164.09, 164.11

See application file for complete search history.

(56) References Cited

U.S. PATENT DOCUMENTS

| | | | | |
|---|---|---|---|---|
| 840,560 A | * | 1/1907 | Farrington et al. | ........... 604/37 |
| 1,211,928 A | * | 1/1917 | Fisher | .......................... 604/40 |
| 3,933,439 A | | 1/1976 | McDonald | |
| 5,372,582 A | | 12/1994 | Skrabal et al. | |
| 5,536,242 A | * | 7/1996 | Willard et al. | ................ 604/30 |

OTHER PUBLICATIONS

Merriam-Webster's Collegiate Dictionary, 10th ed., Merriam-Webster, Incorporated, 2001, 775.*

* cited by examiner

Primary Examiner—Max F. Hindenburg
Assistant Examiner—Jonathan Foreman
(74) Attorney, Agent, or Firm—Dorsey & Whitney LLP

(57) ABSTRACT

A micro perfusion device including a casing, a perfusate supply, an inner cannula forming an inner lumen between a front cannula opening which is distal when the device is subcutaneously positioned and a rear cannula opening, the inner lumen being connected or connectable to the perfusate supply via the rear cannula opening, a perfusion cannula projecting from a lower side of the casing and surrounding the inner cannula, an outer lumen between the inner cannula and the perfusion cannula, a collecting container for the perfusate, and a perfusate outlet connecting the outer lumen to the collecting container, wherein the collecting container has a variable volume and a partial vacuum with respect to a pressure prevailing in the perfusate supply may be generated in the collecting container.

10 Claims, 5 Drawing Sheets

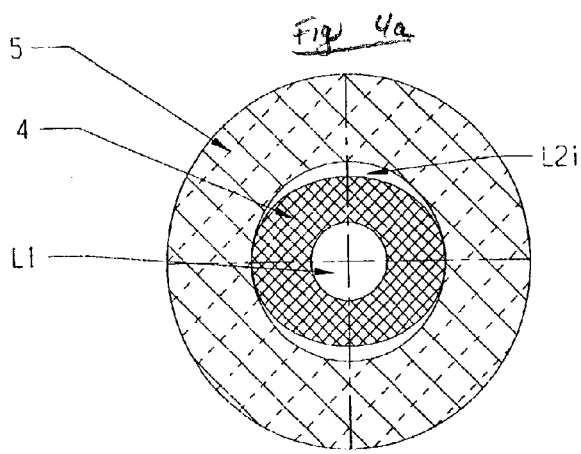
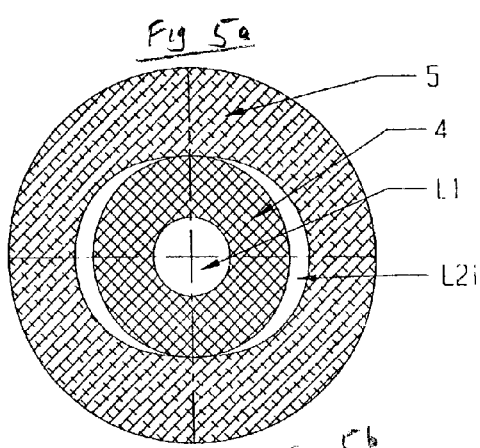
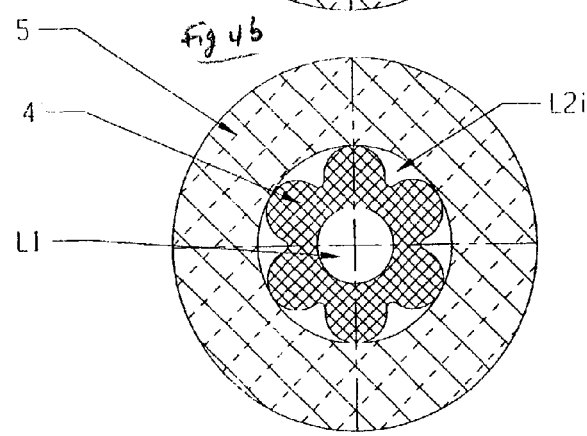
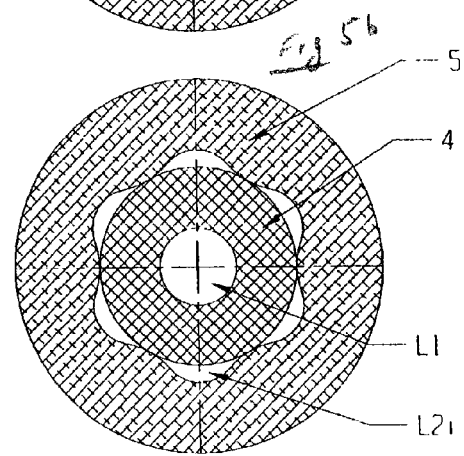
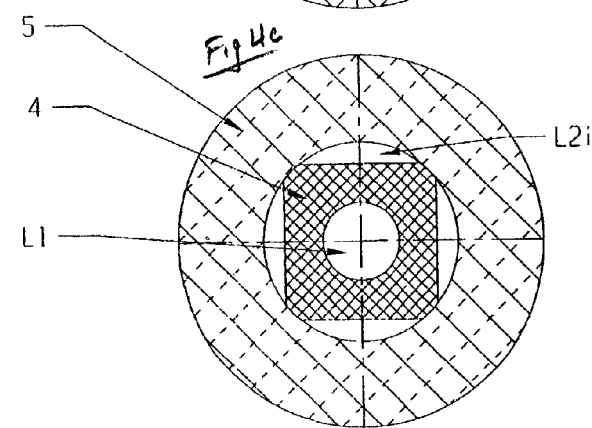
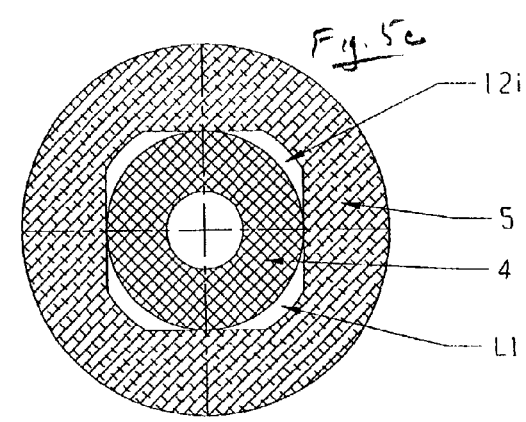
Fig. 4                Fig. 5

MICRO PERFUSION DEVICE COMPRISING A COLLECTING CONTAINER

PRIORITY CLAIM

This is a continuation application of International Patent Application No. PCT/CH01/00111, filed on Feb. 22, 2001, which claims priority to German Patent Application No. 100 08 826, filed on Feb. 25, 2000, both of which are hereby incorporated by reference herein.

BACKGROUND

The invention relates to perfusion devices and methods and, more particularly, to a micro perfusion device comprising a collecting container for obtaining at least one constituent of a body fluid using a subcutaneously positioned perfusion cannula.

A micro perfusion device such as one suitable for use in the present invention comprises a casing, a perfusate supply, an inner cannula, a perfusion cannula, a collecting container and a perfusate outlet. The inner cannula is accommodated by the casing and/or by the perfusion cannula. On a lower side of the casing, the perfusion cannula projects from the casing and surrounds the inner cannula. The inner cannula comprises two cannula openings. The cannula opening which is distal when the device is implanted, i.e., subcutaneously positioned, will be referred to as the front cannula opening, and the other cannula opening which, by contrast, is nearer the casing will be referred to as the rear cannula opening. The inner cannula encloses an inner lumen between its front cannula opening and its rear cannula opening. The inner cannula and the surrounding perfusion cannula form a co-axial flow system comprising the inner lumen and an outer lumen between the inner cannula and the perfusion cannula. A rinsing fluid, called perfusate, is supplied by the perfusate supply up to the rear cannula opening, introduced through the rear cannula opening into the inner lumen, flows through the inner lumen, leaves the inner lumen through the front cannula opening into the surrounding outer lumen (i.e., the lumen of the perfusion cannula) and flows in the outer lumen back towards the casing, enters the outlet and lastly passes through the outlet into the collecting container.

In known perfusion or dialysis devices, the perfusate is conveyed by means of pumps which are arranged selectively or in combination in the perfusate supply or in the perfusate outlet and convey the perfusate into the collecting container via the perfusion supply and the two lumens. Power sources and control systems are provided for such conveying systems.

SUMMARY

It is an object of the invention to provide a micro perfusion device of the type described above in which the perfusate is conveyed in a simplified way.

In one embodiment, the present invention provides a micro perfusion device and a method for its use, wherein the device comprises a casing, a perfusate supply, an inner cannula having an inner lumen between a front cannula opening which is distal when the device is subcutaneously positioned and a rear cannula opening, the inner lumen being connected or connectable to the perfusate supply via the rear cannula opening, a perfusion cannula having a lumen and projecting from a lower side of the casing, the perfusion cannula surrounding the inner cannula to form an outer lumen between the inner cannula and the perfusion cannula, a collecting container for the perfusate, and a perfusate outlet connecting the outer lumen to the collecting container, wherein the collecting container has a variable volume and a partial vacuum with respect to a pressure prevailing in the perfusate supply may be generated in the collecting container.

In one embodiment, the above stated object is addressed by using a variable-volume collecting container in which a partial vacuum may be generated by enlarging the volume and is generated during operation, which suctions the perfusate into the collecting container. The partial vacuum which may be generated is with respect to the perfusate supply. The collecting container is preferably air-tight, though in principle it is only necessary that, when the volume of the collecting container is enlarged, the pressure is equalized through the walls of the collecting container only so slowly that said partial vacuum prevails while the volume of the container is enlarged. Preferably, the partial vacuum continues to exist even if the collecting container is given an expanded end shape in order to then suction in the perfusate from the outer lumen.

The collecting container can be connected to the casing by the outlet. The collecting container can be expanded by an elastic restoring force of a restoring element formed, for example, by an installed pressure spring or an elastically ductile container wall. The restoring element is held pre-tensioned, for example, by a pre-tensioning means acting from without. Releasing the pre-tensioning means releases the restoring element and expands the collecting container as it releases the tension.

In one embodiment, the collecting container is fixed or fixable to the casing via a wall or a part of a wall. Another wall or part of a wall of the container is movable with respect to the casing, such that the collecting container can be expanded by the movement of this container wall relative to the fixed container wall. By fixing the collecting container to the casing, a particularly compact construction of the micro perfusion device is obtained.

In preferred embodiments, the inner cannula protrudes through the casing and is accommodated by the casing so as to be slidable in the longitudinal direction from a front sliding position to a rear sliding position. The collecting container is fixedly connected or connectable to the casing as described above, i.e., at least one wall of the collecting container is fixed to the casing or formed by the casing. The movable wall is connected to the inner cannula by a slaving means. A substantially rigid connection preferably exists between the inner cannula and the slaving means. In principle, a non-sliding and non-pivoting connection with respect to the sliding direction is also sufficient. The connection between the slaving means and the movable wall of the collecting container is also preferably substantially rigid, or there is a connection which allows a pivoting movement between the slaving means and the movable wall of the collecting container, which for preventing jamming may be preferred.

The volume of the collecting container is preferably enlarged by sliding the inner cannula from its front sliding position to its rear sliding position, which also establishes the connection between the perfusate supply and the inner lumen. The connection is established by the rear needle opening coming to rest in the rear sliding position of the inner cannula in the perfusate supply.

The collecting container is preferably formed as a bellows, comprising two container walls which are substantially rigid in themselves and connected to each other by a flexible wall.

Instead of or in addition to conveying by suction in accordance with the invention, conveying by pressure can also be provided for. A perfusate storage container connected to the perfusate supply can be provided as the pressure conveyor, whose volume is reduced by the movement of one container wall towards another container wall, such that a pressure burden relative to the pressure in the perfusate outlet is generated in such a perfusate storage container. The mechanisms described above for enlarging the volume of the collecting container can also be used analogously to reduce the volume of the perfusate storage container.

The micro perfusion device of the invention can advantageously be developed into an autonomic perfusion system, by connecting the perfusate supply to a flexible perfusate storage container or forming the perfusate supply itself as a protrusion of such a storage container. Such a flexible perfusate storage container can advantageously be arranged on or in the casing. When the volume of the collecting container is enlarged, the storage container contracts as it is emptied and so offers no resistance or no practically appreciable resistance to being emptied. The storage container is fluid-proof and preferably also air-tight.

In one preferred application or use, the micro perfusion device in accordance with the invention serves to measure or ascertain the concentration or concentrations of one or more constituents of body fluids. In one case, the at least one constituent of the body fluid is glucose. Preferably, the body fluid together with the perfusate is obtained quite simply by the rinsing process. By using an appropriate perfusate or rinsing fluid, a particular constituent can also be selectively obtained by means of the micro perfusion device in accordance with the invention, in addition to the body fluid rinsed with it.

In a preferred exemplary embodiment, the fluid connection between the perfusate supply and the inner cannula exists in the rear sliding position of the inner cannula. In this case, the perfusate supply is a supply channel formed in the casing. In the rear sliding position, the inner cannula opens into this supply channel via its rear cannula opening. This ensures that the perfusate discharge in the casing is sealed fluid-proof with respect to the perfusate supply. Appropriate sealing means are preferably provided in the casing for this purpose.

The rear cannula opening of the inner cannula and therefore the inner lumen can, however, also be permanently connected to the perfusate supply. For this purpose, a catheter forming the perfusate supply can very simply be placed over the rear end of the inner cannula, which is open-back on its facing side, or otherwise connected fluid-proof to the inner lumen.

The perfusion cannula can in principle be formed by a catheter closed on its surface side, having an open front facing side. However, the perfusion cannula is preferably laterally permeable to the at least one constituent. A perfusion cannula with a permeable surface can be manufactured from a porous material which is permeable to the at least one constituent, the body fluid as a whole or selectively only for the at least one constituent. The permeability can be obtained by perforations formed directly as the perfusion cannula is manufactured, or subsequently incorporated, for example by means of lasers.

If the perfusion cannula is perforated, then the lateral perforation openings of the perfusion cannula are preferably elongated in the longitudinal direction of the cannula, in order to obtain as great a stability against straining as possible. Straining the catheter as it is inserted into the tissue, also known as peal back effect, is thus prevented or at least kept to a minimum. The perforation openings are particularly preferably arranged on gaps or offset with respect to each other, not along a line extending in the longitudinal direction of the perfusion cannula, but in the circumferential direction of the perfusion cannula.

The inner cannula is particularly preferably an injection needle, for example a steel needle, which also serves to subcutaneously position the perfusion cannula. In principle, however, the inner cannula could be formed by a cannula which is not inserted until after the device has been subcutaneously positioned, as in conventional perfusion or dialysis devices.

In order to obtain a perfusion cannula which is as slim as possible, the outer cross-section of the injection needle and the inner cross-section of the perfusion cannula preferably exhibit different shapes, preferably such that the perfusion cannula abuts the injection needle in longitudinal strips, and a longitudinal gap remains between adjacent longitudinal strips. In this form, the perfusion cannula can wrap tightly around the injection needle along its entire length situated in the tissue. A flow cross-section for the perfusate flowing back nonetheless remains between the outer surface area of the injection needle and the inner surface area of the perfusion cannula. In preferred exemplary embodiments, either the injection needle or the perfusion cannula exhibits a cross-section which deviates from the circular form. If, for example, the injection needle exhibits an outer cross-section deviating from the circular form along its implanted length, then the perfusion cannula can exhibit a circular inner cross-section tensed around the needle. Equally, the perfusion cannula can exhibit a non-circular inner cross-section and the injection needle a circular outer cross-section. However, it is also possible for the outer cross-section of the injection needle and the inner cross-section of the perfusion cannula to deviate from the circular form, so long as it is ensured that a sufficient flow cross-section for the purpose of rinsing remains between the needle and the perfusion cannula and that the perfusion cannula surrounds the injection needle, preferably wrapped tightly around it, for the purpose of securely implanting it.

In its rear sliding position, the inner cannula is preferably fixed to the casing in such a way that the rear sliding position or movement into the rear sliding position can be tactilely sensed by someone using the micro perfusion device. The inner cannula can, for example, simply be moved into its rear sliding position against a stopper. The inner cannula is preferably fixed not only against sliding further, beyond the rear sliding position, but also against the inner cannula advancing. The inner cannula is preferably fixed to the casing in its rear sliding position by means of a locking connection, preferably a detachable locking connection. For fixing it, a protrusion, a dent, a slit or the like is preferably formed on the inner cannula. In a preferred exemplary embodiment, the rear cannula opening is used for the purpose of the locking connection.

In one preferred embodiment, the micro perfusion device of the present invention is not only used to obtain at least one constituent of the body fluid, but substantially simultaneously serves as a miniature measuring means or at least as an electrode platform for a measuring means. The measuring means preferably serves to measure or ascertain the concentration of the at least one constituent in the body fluid. When used as an electrode platform, with or without an integrated measuring means, an electrode of the measuring means is formed on the lower side of the casing via which the casing sits on the tissue. A working electrode of the measuring means is electrically connected to the discharged rinsing fluid and is preferably arranged in the discharge channel of the casing. The electrode formed on the lower side of the casing forms the counter electrode to this working electrode and serves to measure an electrical current and/or an electrical potential. Preferably, a sufficiently large bearing area is formed on the lower side of the casing for the counter electrode to be able to form a sufficiently large contact area with the tissue and simultaneously be used as a reference electrode. Furthermore, the lower side can fulfil an adhesive function, for adhering to the skin.

When it is formed as a miniature measuring means, a sensor is arranged in the casing of the micro perfusion device, said sensor preferably measuring the concentration of the at least one constituent in the body fluid. More precisely, the concentration in the perfusate flowing back is measured and from this, the concentration in the body fluid is ascertained. The sensor is preferably arranged as near to the sampling point as possible, but outside the body, on or in the casing, in the outlet. The perfusate flowing back preferably comes into measuring contact with the sensor immediately downstream of the outer lumen. The sensor is preferably inserted or recessed into a side wall of the outlet and preferably does not protrude out of the wall, in order to keep the flow resistance to a minimum. Preferably, no parts of the casing wall or only as much casing wall as is necessary to securely attach the sensor is arranged in the flow path between the outer lumen and the sensor.

Although forming it with an integrated sensor, as an electrode platform and as an electrode platform with an integrated sensor are particularly advantageous in combination with the micro perfusion device in accordance with the invention, each of these formations, in particular forming an electrode on the lower side of the casing, can also be realized with all conventional micro perfusion devices.

BRIEF DESCRIPTION OF THE DRAWINGS

FIG. 1a is an expanded view of a portion of FIG. 1;

FIG. 4, including FIGS. 4a–c, depicts injection needles with non-circular outer cross-sections;

FIG. 5, including FIGS. 5a–c, depicts perfusion cannulae with non-circular inner cross-sections;

DETAILED DESCRIPTION

Figure 1:
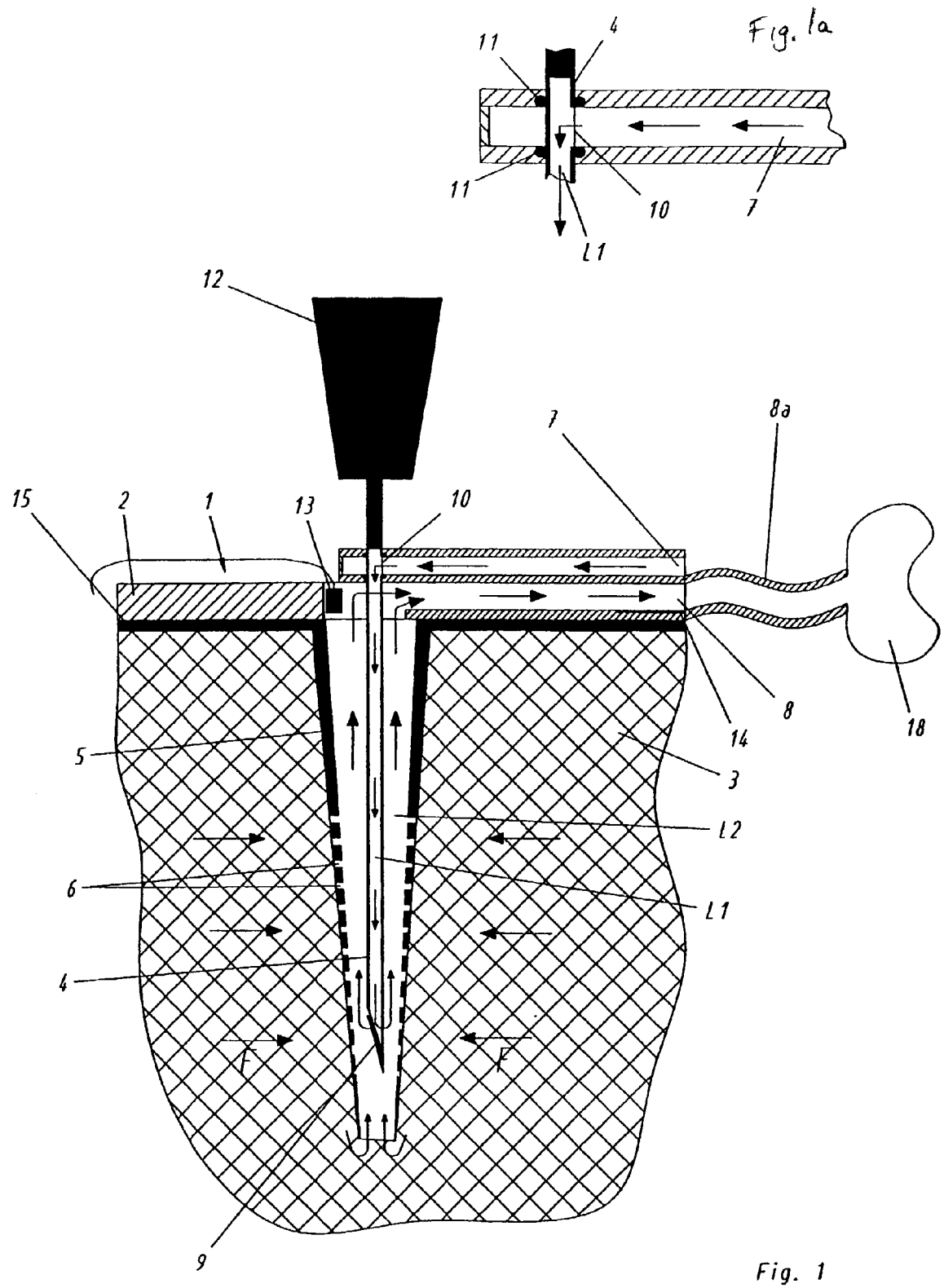
FIG. 1 depicts a micro perfusion device in accordance with a first exemplary embodiment, comprising an integrated sensor and integrated electrodes for a measuring means.

FIG. 1 shows an implanted micro perfusion device in a longitudinal section. The device comprises a casing 1 with a bearing disc 2, onto the lower side of which an adhesive patch 15 is attached. A flexible, perforated perfusion cannula 5 projects perpendicularly from the lower side of the bearing disc 2. The perfusion cannula 5 concentrically surrounds an inner cannula 4 protruding into it. The inner cannula 4 is formed as an injection needle. The injection needle 4 is formed in the manner of injection needles such as are known from catheter heads for infusing insulin. The injection needle 4 is formed by a slim, straight hollow cylinder having a front needle opening 9 at its distal, front facing end and a rear needle opening 10 in the surface of the injection needle 4. The injection needle 4 does not comprise any other openings. The injection needle 4 encloses an inner lumen L1 between its two openings 9 and 10. An outer lumen L2, in the form of an annular gap, is formed between the injection needle 4 and the perfusion cannula 5.

In the casing 1, an outlet in the form of a discharge channel 8 and a perfusate supply lying above it, in the form of a supply channel 7, are formed in the bearing disc. The injection needle 4 is accommodated slidably in the casing, guided in a straight line in the longitudinal direction. The linear guide is formed by a through-bore which projects through the casing 1 from an upper side to the opposite lower side. In this way, the injection needle 4 projects through both the supply channel 7 and the discharge channel 8. Referring to FIG. 1a, in the supply channel 7, two sealing rings 11 are inserted into two recesses, each encircling the through-bore in the inner wall of the supply channel 7, said sealing rings 11 surrounding the injection needle 4 in a pressure force seal. In a rear sliding position of the injection needle 4, shown, the rear needle opening 10 comes to rest between the two sealing rings 11. In this way, a fluid-proof connection between the supply channel 7 and the inner lumen L1 is created in the rear sliding position of the injection needle 4, and the supply channel 7 and discharge channel 8 are constantly separated, fluid-proof.

In the rear sliding position of the injection needle 4, the sealing rings 11 simultaneously establish a locking connection between the injection needle 4 and the casing 1. In the locking position, i.e. in the rear sliding position, the two sealing rings 11 are pressed into the rear needle opening 10. In this way, a locking or latching effect is achieved. The rear needle opening 10 extends in the longitudinal direction of the injection needle 4 over such a length that both sealing rings 11 come to rest in the rear needle opening 10 and one each of the two sealing rings 11 presses on a rear and a front opening rim, respectively. For providing the locking connection, it would in principle be sufficient if only one of the sealing rings 11 came to rest behind the rear or front rim of the rear needle opening 10, in the rear sliding position. However, pressing against both the rear rim and against the opposite, front opening rim of the rear needle opening 10 creates a locking connection which prevents the injection needle 4 from being unintentionally slid in either sliding direction. The fluid connection between the supply channel 7 and the injection needle 4, as well as the locking connection between the casing 1 and the injection needle 4, are shown again in a separate, enlarged detail in FIG. 1a.

In order to facilitate manually sliding the injection needle 4, the injection needle 4 is provided with a needle grip 12 on its rear end protruding out of the casing 1.

FIG. 1 shows the micro perfusion device in its operational state during micro perfusion, wherein the injection needle 4 is situated in its rear sliding position in the casing 1. Before the perfusion cannula 5 is implanted or positioned in the tissue 3, the injection needle 4 projects through the perfusion cannula 5 in a front sliding position. In this initial state, the tip of the injection needle 4 including the front needle opening 9 lies beyond the front end of the perfusion cannula 5. In this initial state, the needle grip 12 is pressed up against the surface of the casing 1. In order to position the perfusion cannula 5, the injection needle 4 and the perfusion cannula 5, which at least at its front end wraps around the injection needle 4, are pierced through the skin and inserted into the tissue 3, up to the position shown in FIG. 1. In this position, the bearing disc 2 of the casing 1 lies flat on the skin via its lower side. The adhesive patch 15 attached to the lower side of the bearing disc 2 forms an adhesive area with the skin. By pressing the casing 1 against the skin, an adhesive connection is established. In order to perform micro perfusion, the injection needle 4 is retracted to the rear sliding position shown in FIG. 1, once the casing 1 has been positioned and attached. The micro perfusion device is then ready for micro perfusion to be performed, in order to obtain the at least one constituent of the body fluid.

The perfusion cannula 5 is perforated with perforation openings 6 in a surface area between its front distal end and its rear proximal end bordering the casing 1. A non-perforated surface area remains in front of the perforated area at the front end of the perfusion cannula 5. The perfusion cannula 5 is also non-perforated in the area of its rear end. On its facing side, the perfusion cannula 5 opens forwards. When the perfusion cannula 5 is rinsed, so-called open flow micro perfusion arises. A perfusate is guided through a connected supply catheter into the supply channel 7 of the casing 1, enters the hollow injection needle 4 through its rear needle opening 10, flows through the injection needle 4 and emerges into the perfusion cannula 5 through the front distal needle opening 9 at the tip of the needle. Having emerged, the perfusate in the outer lumen L2 between the outer surface of the injection needle 4 and the perfusion cannula 5 flows back towards the casing 1. As the perfusate flows back, body fluid F is suctioned in through the perforation openings 6 due to a resultant jet effect in the outer lumen L2 and carried along in the back flow of perfusate, and selectively, the body fluid constituent to be obtained or a number of body fluid constituents are absorbed through the perforation openings 6 due to a concentration gradient between the body fluid F and the perfusate and carried along in the back flow of perfusate. The perfusate flowing back passes from the outer lumen L2 into the discharge channel 8 via a fluid connection formed in the casing 1 and then flows through a discharge catheter 8a connected to the discharge channel 8, into a collecting container 18.

The perfusate is conveyed by means of suction from the perfusate supply into the collecting container 18. It is conveyed by suction by generating a partial vacuum in the collecting container 18. For this purpose, the collecting container 18 is formed as a variable-volume collecting container 18. It comprises an elastic container wall which in an initial state of the micro perfusion device is pressed or folded together against its own elastic restoring forces. The collecting container 18 is held in its pressed or folded together state by a pre-tensioning means. To convey the perfusate by suction, the latch is released and the collecting container 18 expands due to the elastic restoring forces of the container wall. The container wall of the collecting container 18 is air-tight, at least to the extent that the pressure does not equalize through the flexible container wall, or at least significantly delayed in comparison with the pressure equalization caused by the perfusate flowing in. The collecting container 18 can expand or begin to expand immediately before the fluid connection is established between the inner lumen L1 and the supply channel 7. It can also begin to expand in the smallest possible time interval, after the fluid connection has been established.

An external collecting container 18 is provided in the exemplary embodiment in FIG. 1. The same flexible collecting container 18 can, however, also be directly arranged on the casing 1 or fixed to it, for example via an adhesive connection with the upper side of the casing 1. In this case, a pre-tensioning means for pre-tensioning the collecting container 18 in its pressed or folded together state can advantageously also be formed on the surface of the casing 1.

In the casing 1, a miniature sensor 13 is arranged in a flow cross-section of the perfusate flowing back. The sensor 13 is arranged in the discharge channel 8 in the casing 1, in a flow cross-section immediately downstream of the perfusion cannula 5. The sensor 13 is not, however, implanted but is situated in a flow cross-section as near as possible to the body, i.e. as near as possible to the sampling point, outside the tissue 3. In one embodiment, it can still be inserted, for example clipped, into the casing 1 even subsequently, i.e., after the micro perfusion device has been positioned.

The micro perfusion device serves not only as a sensor platform, but simultaneously also serves as an electrode platform for a measuring means. A working electrode 14 is formed in the casing 1 on an inner wall of the discharge channel 8 or forms an area of the inner wall. The adhesive patch 15 is itself electrically conductive and is electrically connected to the skin. It serves the measuring means as a counter electrode to the working electrode 14. The bearing area of the adhesive patch 15 is preferably sufficiently large that it also simultaneously forms a reference electrode.

Figure 2:
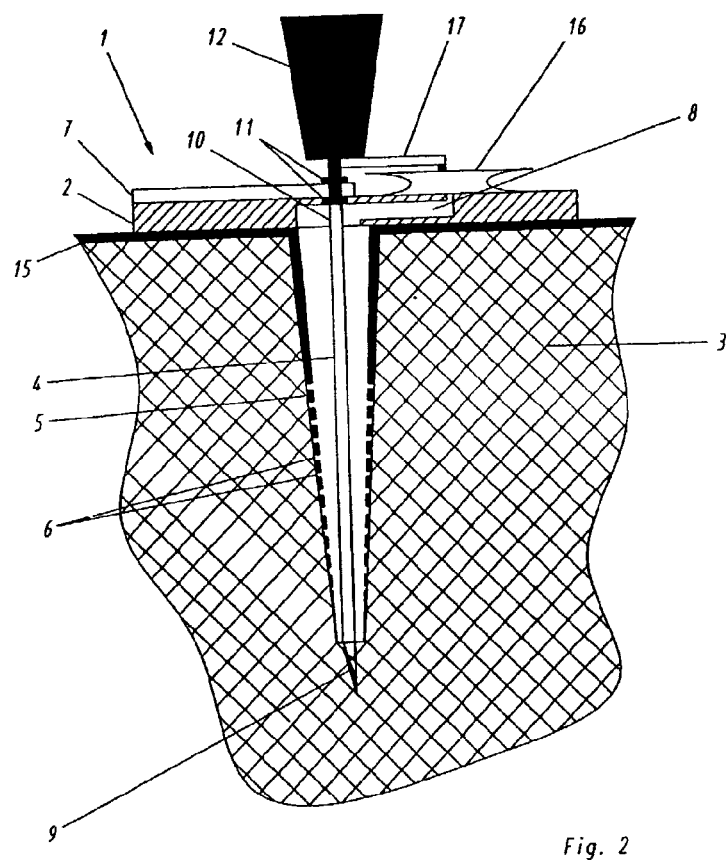
FIG. 2 depicts a micro perfusion device in accordance with a second exemplary embodiment, before perfusion.
Figure 3:
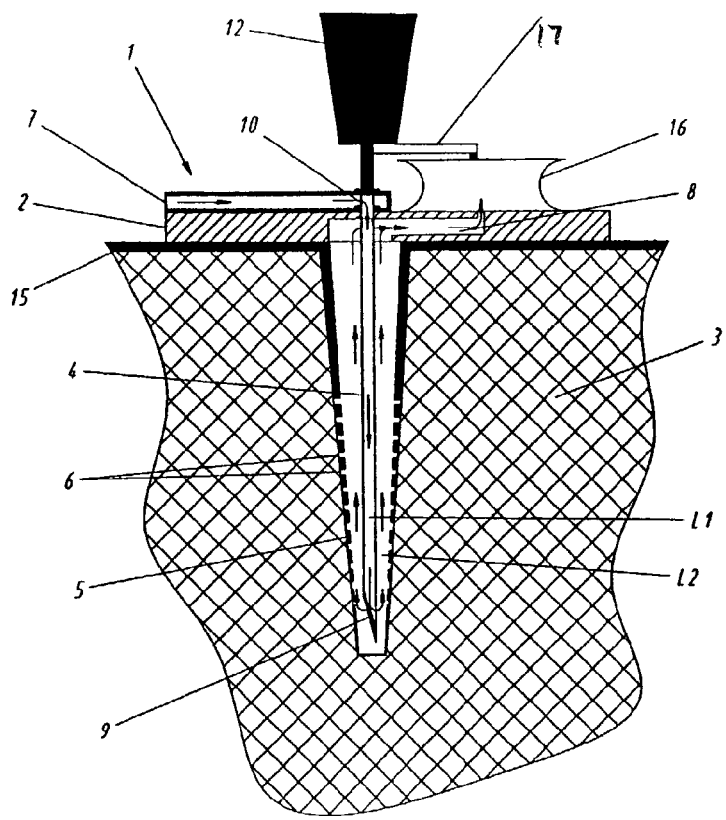
FIG. 3 depicts the micro perfusion device in accordance with the second exemplary embodiment, during perfusion.

FIGS. 2 and 3 show a micro perfusion device which conveys by suction, in a preferred embodiment. The device does not comprise an integrated sensor or integrated electrodes, but could be formed like the device in the embodiment of FIG. 1. It further differs from the embodiment of FIG. 1 in the position of the supply channel 7 relative to the discharge channel 8 and in the course of the discharge channel 8. It otherwise substantially identically corresponds to the micro perfusion device of FIG. 1.

FIG. 2 shows the micro perfusion device in its initial state before it is positioned in the tissue, the injection needle 4 assuming its front sliding position with respect to the casing 1 and the perfusion cannula 5. The micro perfusion device is also still in this state after it has been positioned in the tissue, until the injection needle 4 is retracted right up to its rear sliding position.

FIG. 3 shows the injection needle 4 in its rear sliding position. By retracting the injection needle 4 some way behind the front end of the perfusion cannula 5, a suitable co-axial flow system is created for the subsequent perfusion, as already described by way of the first embodiment.

The micro perfusion device of the embodiment in FIGS. 2 and 3 comprises an integrated collecting container 16. The collecting container 16 is fixed to the upper side of the casing 1 via a lower container wall, preferably by means of an adhesive connection. The collecting container 16 comprises two container walls which are rigid in themselves, namely the lower container wall cited and opposite it, an upper container wall. These two container walls which are rigid in themselves are connected to each other by a flexible container wall. In this way, the collecting container 16 is realized as bellows.

The discharge channel 8 flows into the collecting container 16 on the upper side of the casing 1. A connection which is sufficiently air-tight for conveying by suction exists between the discharge channel 8 and the hollow space of the collecting container 16.

The collecting container 16 is arranged in the immediate vicinity of the injection needle 4 which protrudes beyond the upper side of the casing 1. Seen from the injection needle 4, the supply channel 7 is guided to a side of the casing 1 opposite the collecting container 16.

A slaving means 17 projects perpendicularly from the injection needle 4. The slaving means 17 is formed in one piece as a rigid stay and is completely rigid, i.e., it is immovably attached to the injection needle 4. The slaving means 17 projects perpendicularly from the injection needle 4 beyond the upper container wall of the collecting container 16. It is likewise rigidly attached at its free end to the upper side of the upper container wall. Attaching it by means of a pivoting joint, which pivots with respect to the sliding direction of the injection needle 4, would also be conceivable.

In the initial state shown in FIG. 2, the upper container wall is tightly spaced with respect to the fixed lower container wall. The collecting container 16 is folded together and exhibits its smallest inner volume. Once subcutaneously positioned, as described above by way of FIG. 1, the injection needle 4 is retracted to its rear sliding position, thus establishing the fluid connection between the inner lumen L1 and the supply channel 7. At the same time as the injection needle 4 is slid, the upper container wall of the collecting container 16 is slaved by means of the slaving means 17 and the collecting container 16 thus expands until it ultimately exhibits its largest inner volume, once the injection needle 4 is in its rear sliding position. This state is shown in FIG. 3. The container walls of the collecting container 16 are sufficiently airtight that a partial vacuum is maintained relative to the pressure which prevails in the supply channel 7. This partial vacuum suctions in the perfusate from the supply channel 7, through the two lumens L1 and L2 and the discharge channel 8, into the collecting container 16. The perfusate comprising the thus absorbed body fluid or, as the case may be, just the selectively absorbed constituent of the body fluid, is then available in the collecting container 16, to be measured. As already mentioned, a sensor of a measuring means can be arranged in the discharge channel 8, as in the first embodiment, preferably as near as possible to the body, i.e., as near as possible to the sampling point, but outside the tissue. Such a sensor can instead, however, also be arranged in the collecting container 16.

FIGS. 4, including FIGS. 4*a–c*, and 5, including FIGS. 5*a–c*, show combinations of injection needles 4 and perfusion cannulae 5, whose cross-sectional shapes are respectively adapted to each other such that a sufficient flow cross-section always remains in the outer lumen L2 over the entire flow length of the fluid flowing back, and the perfusion cannula 5 nonetheless tightly surrounds or wraps around the injection needle 4. In the cross-section combinations in FIG. 4, the inner cross-section of the perfusion cannula 5 in each case is circular in its neutral, untensed state, while the outer cross-section of the injection needle 4 deviates from the circular cross-sectional shape. In the cross-section combinations in FIG. 5, by contrast, the outer cross-section of the injection needle 4 is circular, and the inner cross-section of the perfusion cannula 5 deviates from the circular form. When installed, the perfusion cannula 5 is also tensed around the injection needle 4 in its neutral state. In this way, partial lumens L2*i* through which the perfusate can flow back are formed along and distributed around the injection needle 4, between the points at which the perfusion cannula 5 presses on the injection needle 4. By forming the outer cross-section of the injection needle 4 and the inner cross-section of the perfusion cannula 5 such that the perfusion cannula 5 only presses on the injection needle 4 in longitudinal strips and partial lumens 2L*i* remain between the pressure strips, the perfusion cannula 5 can be tensed around the injection needle 4 over its entire implanted length or at least over a front, partial length. The injection needle 4 thus supports the perfusion cannula 5, which is advantageous when piercing the skin and inserting it further into the tissue.

Figure 6:
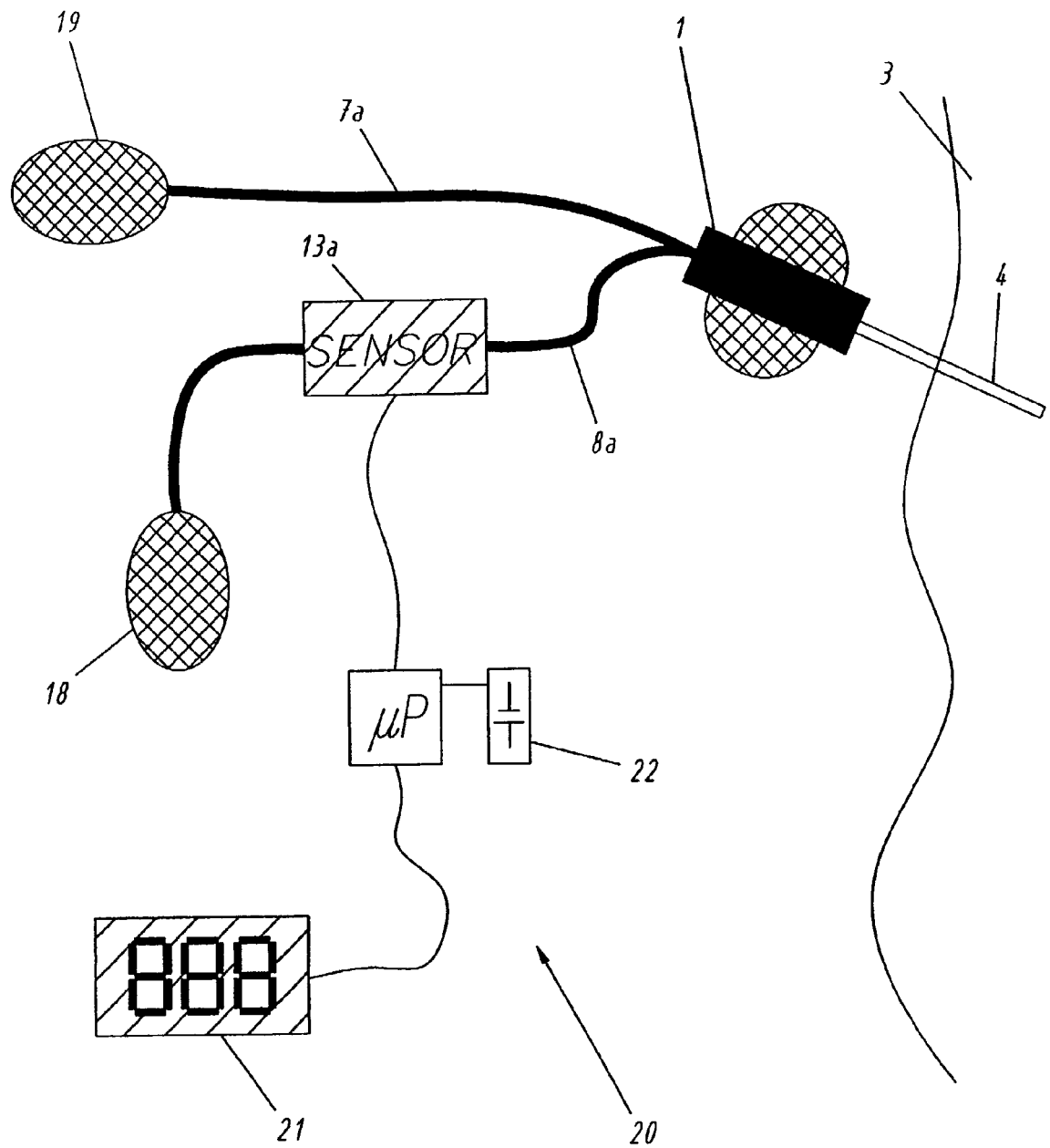
FIG. 6 depicts a micro perfusion device with a connected measuring means, in a schematic representation.

FIG. 6 shows a perfusion device, comprising a connected measuring and evaluating means, in a schematic representation. The micro perfusion device, which is shown only schematically and formed, for example, by a device in accordance with FIG. 1, is connected to a supply catheter 7*a* and a discharge catheter 8*a*. By expanding the collecting container 18, a perfusate is conveyed from a flexible storage container 19, through the supply catheter 7*a*, into the injection needle 4. The perfusate flowing back is supplied to an external sensor 13*a* and then suctioned into the collecting container 18, from which it is disposed of. The perfusate flowing back to the sensor 13*a* contains at least one body fluid constituent whose concentration is to be ascertained by measurement. If this constituent is glucose, then the sensor 13*a* is a glucose sensor. The measuring signals from the sensor 13*a* are supplied to an evaluation means 20 which ascertains the concentration of the at least one constituent from them and displays this on a display 21. In the embodiment in FIG. 6, the micro perfusion device is positioned in the tissue of the lower arm (not shown). The sensor 13*a*, the collecting container 18, a part of the evaluation means 20 and the display 21 are collectively accommodated in a lower arm unit. A suitable microprocessor of the evaluation means 20 and a battery 22 are accommodated together in a belt unit and operably connected to the lower arm unit in order to exchange data and supply the lower arm unit with power. The evaluation unit 20, in particular the microprocessor, evaluates the measuring signals from the sensor 13*a*.

The sensor 13*a* can advantageously be arranged integrated in the casing 1 of the device, preferably as near to the sampling point as possible.

In each of the examplary embodiments described herein, the inner cannula 4 is formed by an injection needle. The double function of the inner cannula 4, namely as an injection needle on the one hand and as a means of forming the inner lumen L1 on the other, represents a preferred embodiment of the inner cannula 4. This is not, however, absolutely necessary for the purpose of the invention. The inner cannula can also be formed flexible, in particular bendable, such that it is no longer suitable as an injection needle. Forming a flexible inner cannula 4 in this way can also be realized in the embodiments described above. If the inner cannula 4 serves as an activating means for expanding a collecting container, however, then it is sufficiently dimensionally stable at least in its rear area, in which a slaving means projects from the inner cannula 4 as in the second embodiment, in order that a good guide is maintained in the casing when the collecting container is expanded.

Figure 7:
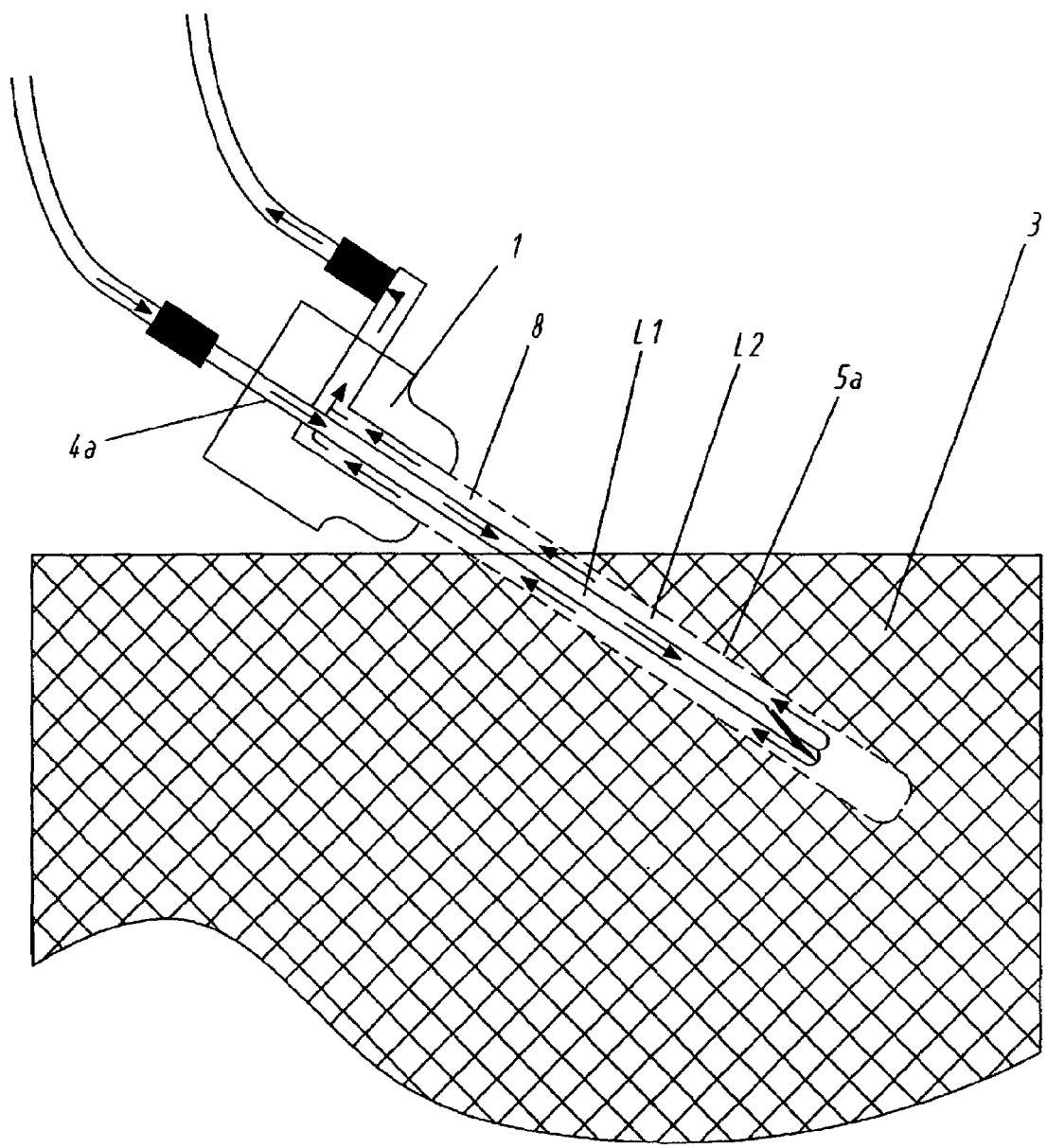
FIG. 7 depicts a micro perfusion device in accordance with a third exemplary embodiment.

FIG. 7 shows a micro perfusion device such as is known in principle from the prior art. The inner cannula 4*a* is formed as a flexible catheter, which has been inserted into the perfusion cannula 5*a* once the perfusion cannula 5*a* has been positioned. The perfusion cannula 5*a* is positioned by means of an injection needle which surrounds the perfusion cannula 5*a* or is enclosed by the perfusion cannula 5*a*, and which is removed again once perfusion cannula 5*a* has been positioned in the tissue 3. The perfusion cannula 5*a* is open at its front end and perforated in its surface area.

The discharge channel 8, however, flows into a collecting container formed as a variable-volume collecting container in accordance with the invention, or is connected to such a collecting container via a discharge catheter. The perfusate is conveyed through the perfusion system by suction caused by expanding the collecting container. A collecting container 18 such as in the embodiment in FIG. 1 can be used with the micro perfusion device of this third embodiment.

In the foregoing description embodiments of the invention have been presented for the purpose of illustration and description. They are not intended to be exhaustive or to limit the invention to the precise forms disclosed. Obvious modifications or variations are possible in light of the above teachings. The embodiments were chosen and described to illustrate the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A micro perfusion device comprising a collecting container, for obtaining at least one constituent of a body fluid using a subcutaneously positioned perfusion cannula, said device comprising:
   a) a casing;
   b) a perfusate supply;
   c) an inner cannula, forming an inner lumen between a front cannula opening which is distal when the device is subcutaneously positioned and a rear cannula opening, said inner lumen being connected or connectable to said perfusate supply via said rear cannula opening, said inner cannula being accommodated by said casing so as to be slidable in the longitudinal direction from a front sliding position to a rear sliding position and said rear cannula opening being formed in a surface area of said inner cannula;
   d) a sealing ring surrounding said inner cannula in said casing under pressure and, in said rear sliding position of said inner cannula, pre-latching into said rear cannula opening;
   e) a perfusion cannula, projecting from a lower side of said casing and surrounding said inner cannula, an outer lumen remaining between said inner cannula and said perfusion cannula;
   f) a collecting container for said perfusate; and
   g) an outlet for said perfusate, connecting said outer lumen to said collecting container; wherein said collecting container is a variable-volume collecting container and a partial vacuum with respect to a pressure prevailing in said perfusate supply is generated in said collecting container.

2. A micro perfusion device comprising a collecting container, for obtaining at least one constituent of a body fluid using a subcutaneously positioned perfusion cannula, said device comprising:
   a) a casing;
   b) a perfusate supply;
   c) an inner cannula, forming an inner lumen between a front cannula opening which is distal when the device is subcutaneously positioned and a rear cannula opening, said inner lumen being connected or connectable to said perfusate supply via said rear cannula opening;
   d) the perfusion cannula, projecting from a lower side of said casing and surrounding said inner cannula, an outer lumen remaining between said inner cannula and said perfusion cannula;
   e) a collecting container for said perfusate;
   f) an outlet for said perfusate, connecting said outer lumen to said collecting container; wherein said collecting container is a variable-volume collecting container and a partial vacuum with respect to a pressure prevailing in said perfusate supply is generated in said collecting container; and
   g) a sensor of a measuring means, for measuring the concentration of the at least one constituent of said body fluid, the sensor being arranged in or on said casing, in said outlet.

3. The micro perfusion device as set forth in claim 2, wherein said sensor is arranged in an area of said outlet bordering said outer lumen.

4. The micro perfusion device as set forth in claim 2, wherein:
   the measuring means comprises a working electrode and a counter electrode; and
   said counter electrode is formed on a lower side of said casing which contacts a surface of the tissue once said inner cannula and said perfusion cannula have been positioned.

5. The micro perfusion device as set forth in claim 4, wherein said working electrode is formed in said outlet.

6. A micro perfusion device comprising a collecting container, for obtaining at least one constituent of a body fluid using a subcutaneously positioned perfusion cannula, said device comprising:
   a) a casing;
   b) a perfusate supply;
   c) an inner cannula, forming an inner lumen between a front cannula opening which is distal when the device is subcutaneously positioned and a rear cannula opening, said inner lumen being connected or connectable to said perfusate supply via said rear cannula opening;
   d) the perfusion cannula, projecting from a lower side of said casing and surrounding said inner cannula, an outer lumen remaining between said inner cannula and said perfusion cannula;
   e) a collecting container for collecting and holding said perfusate;
   f) and an outlet for said perfusate, connecting said outer lumen to said collecting container; wherein
   g) said collecting container is a variable-volume collecting container having an elastic container wall that includes a pre-tensioning means for holding the container in a compressed state.
   h) and a partial vacuum with respect to a pressure prevailing in said perfusate supply is generated in said collecting container.

7. The device as set forth in claim 6, wherein the collecting container is substantially air-tight.

8. The micro perfusion device as set forth in claim 6, wherein the partial vacuum is generated by enlarging the volume of said collecting container, said partial vacuum suctioning said perfusate from said outer lumen into said collecting container.

9. The micro perfusion device as set forth in claim 6, wherein:
   said inner cannula is accommodated by said casing so as to be slidable in the longitudinal direction from a front sliding position to a rear sliding position; and
   said inner cannula is an injection needle, and in its front sliding position protrudes from said perfusion cannula and in its rear sliding position protrudes beyond said perfusion cannula.

10. The micro perfusion device as set forth in claim 6, wherein said perfusate supply is connected to a variable-volume perfusate storage container.

* * * * *